United States Patent
Isozumi et al.

(10) Patent No.: US 12,133,822 B2
(45) Date of Patent: Nov. 5, 2024

(54) ASSISTANCE SYSTEM

(71) Applicant: FUJI CORPORATION, Chiryu (JP)

(72) Inventors: Joji Isozumi, Chiryu (JP); Satoshi Shimizu, Chiryu (JP)

(73) Assignee: FUJI CORPORATION, Chiryu (JP)

( * ) Notice: Subject to any disclaimer, the term of this patent is extended or adjusted under 35 U.S.C. 154(b) by 796 days.

(21) Appl. No.: 17/264,587

(22) PCT Filed: Aug. 1, 2018

(86) PCT No.: PCT/US2018/044846
§ 371 (c)(1),
(2) Date: Jan. 29, 2021

(87) PCT Pub. No.: WO2020/027833
PCT Pub. Date: Feb. 6, 2020

(65) Prior Publication Data
US 2021/0330528 A1    Oct. 28, 2021

(51) Int. Cl.
*A61G 7/10*    (2006.01)
*A61B 5/00*    (2006.01)
(Continued)

(52) U.S. Cl.
CPC .............. *A61G 7/10* (2013.01); *A61B 5/4803* (2013.01); *A61B 5/7405* (2013.01); *G16H 10/60* (2018.01);
(Continued)

(58) Field of Classification Search
CPC .... A61G 7/10; A61G 7/1001; A61G 2203/18; A61G 1/00; A61B 5/4803; A61B 5/7405;
(Continued)

(56) References Cited

U.S. PATENT DOCUMENTS 8,521,538 B2 * 8/2013 Laughery ................ G10L 15/22
704/275
8,924,218 B2    12/2014 Corpier et al.
(Continued)

FOREIGN PATENT DOCUMENTS

JP    7-49695 A    2/1995
JP    2008-73501 A    4/2008
(Continued)

OTHER PUBLICATIONS

International Search Report issued on Oct. 16, 2018 in PCT/US2018/044846 filed on Aug. 1, 2018.

*Primary Examiner* — David R Hare
*Assistant Examiner* — Deborah Talitha Gedeon
(74) *Attorney, Agent, or Firm* — Oblon, McClelland, Maier & Neustadt, L.L.P.

(57) ABSTRACT

An assistance system includes an assistance device configured to assist movement of a care receiver; a microphone provided on the assistance device; a speech analyzer configured to analyze speech of at least one of a caregiver or the care receiver included in sound data acquired by the microphone and acquire information related to an action; an echo (Continued)

analyzer configured to analyze an echo included the sound data and acquire information related to a location; and an action history information generator configured to generate action history information of at least one of the caregiver or the care receiver based on the information related to the action and the information related to the location.

7 Claims, 8 Drawing Sheets

(51) Int. Cl.
*B25J 11/00* (2006.01)
*G16H 10/60* (2018.01)
*G16H 80/00* (2018.01)

(52) U.S. Cl.
CPC ............... *G16H 80/00* (2018.01); *A61B 5/70* (2013.01); *A61B 5/7207* (2013.01); *A61B 5/749* (2013.01); *A61G 2203/18* (2013.01); *B25J 11/0005* (2013.01)

(58) Field of Classification Search
CPC ........... A61B 5/7415; A61B 5/74; A61B 5/70; A61B 5/7207; A61B 5/7271; A61B 5/7275; A61B 5/7278; A61B 5/7282; A61B 5/749; B25J 11/0005; B25J 11/009; B25J 11/001; G16H 80/00; G16H 10/60
See application file for complete search history.

(56) References Cited

U.S. PATENT DOCUMENTS

| 9,116,230 | B2 | 8/2015 | Vartanian et al. | |
|---|---|---|---|---|
| 9,839,735 | B2 | 12/2017 | Tanenbaum et al. | |
| 2008/0147397 | A1* | 6/2008 | Konig | G10L 21/02 |
| | | | | 704/E15.04 |
| 2010/0192296 | A1* | 8/2010 | Clough | B66D 3/20 |
| | | | | 5/83.1 |
| 2016/0163168 | A1* | 6/2016 | Brav | G08B 29/188 |
| | | | | 381/56 |
| 2017/0143565 | A1* | 5/2017 | Childs | A61G 7/053 |
| 2017/0340498 | A1* | 11/2017 | Tessmer | A61G 13/104 |

FOREIGN PATENT DOCUMENTS

| JP | 2009-134403 A | | 6/2009 | |
|---|---|---|---|---|
| JP | WO2018/047326 A1 | | 7/2019 | |
| KR | 20150041281 A | * | 5/2017 | |
| KR | 20170051994 A | * | 5/2017 | |
| WO | WO-2017141336 A1 | * | 8/2017 | ............... A61G 7/10 |

* cited by examiner

ASSISTANCE SYSTEM

TECHNICAL FIELD

The present application relates to an assistance system.

BACKGROUND ART

In a care facility, various types of assistance are given to a care receiver. Patent literature 1 discloses an assistance device that assists a transfer operation of a care receiver. During this transfer operation assistance, the assistance device, after having completed a standing operation of raising a rear end portion of a seated care receiver from a seat, performs direction changing and then performs a sitting operation of lowering the rear end portion of the care receiver. By this, the care receiver is, for example, moved from a bed to a wheelchair.

CITATION LIST

Patent Literature

Patent literature 1: JP-A-2008-073501

BRIEF SUMMARY

Problem to be Solved

In order to provide appropriate care in a care facility and the like, it is desired to understand the contents of an assistance operation that a care receiver receives. However, setting up cameras at a care facility is not desirable from the point of view of protecting the privacy of care receivers and other people.

An object of the present disclosure is to provide an assistance system for providing more appropriate care to a care receiver by allowing an assistance operation to be understood while protecting the privacy of care receivers and caregivers.

Means for Solving the Problem

Disclosed herein is an assistance system including: an assistance device configured to assist movement of a care receiver; a microphone provided on the assistance device; a speech analyzer configured to analyze speech of at least one of a caregiver or the care receiver included in sound data acquired by the microphone and acquire information related to an action; an echo analyzer configured to analyze an echo included the sound data and acquire information related to a location; and an action history information generator configured to generate action history information of at least one of the caregiver or the care receiver based on the information related to the action and the information related to the location.

Advantageous Effects

According to the configuration of such an assistance system, because an image of assisting the care receiver is not stored, it is possible to protect the privacy of the care receiver and the caregiver. Also, because an action history is recorded for at least one of the care receiver and the caregiver, it is possible to understand an assistance operation for the care receiver and to assist in providing more appropriate care.

DESCRIPTION OF EMBODIMENTS

1. Overview of Assistance System 1

Figure 1:
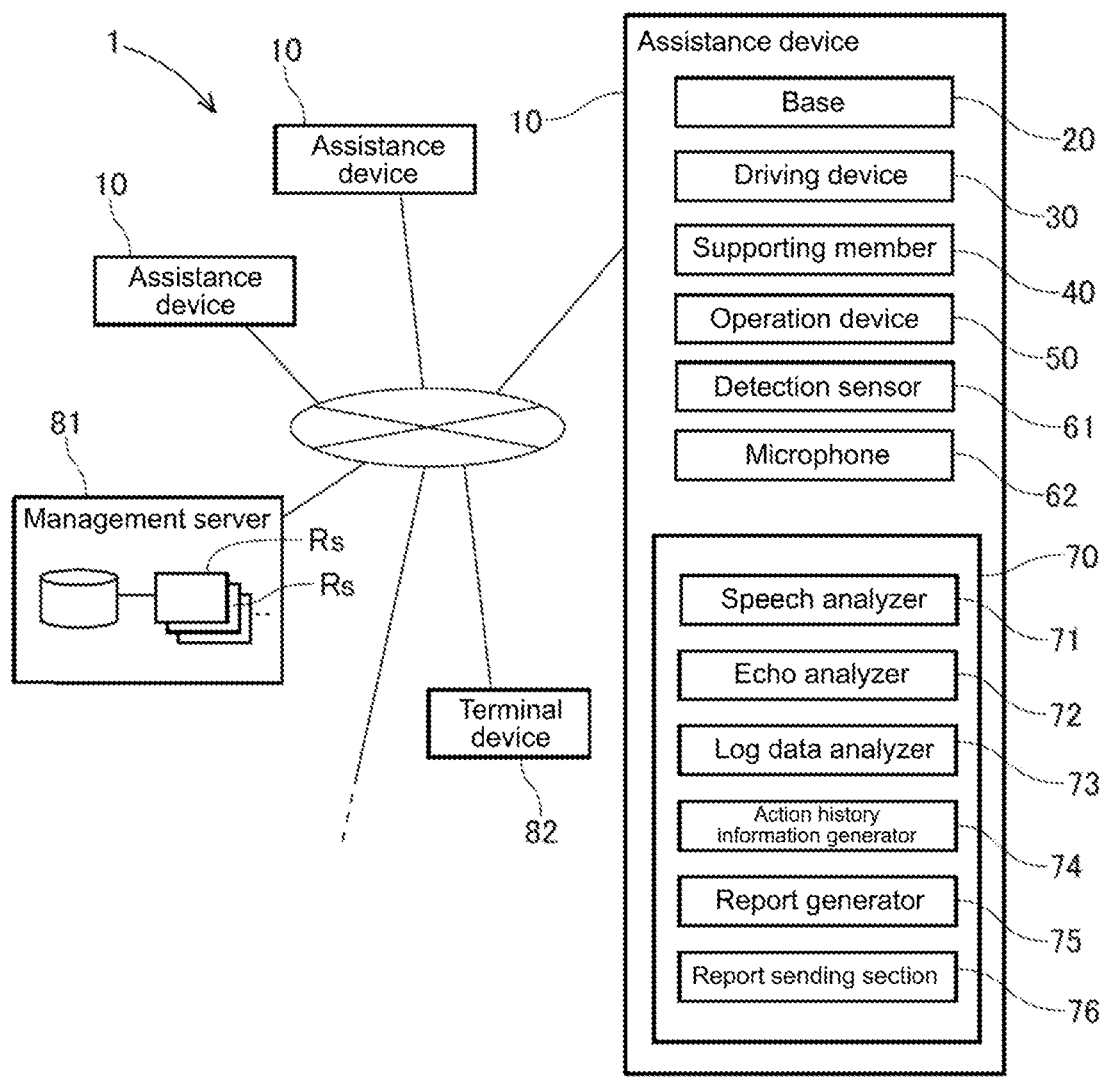
FIG. 1 is a schematic diagram showing an assistance system of an embodiment.

As shown in FIG. 1, assistance system 1 is provided with assistance device 10, management server 81, and terminal device 82. Multiple assistance devices 10 can be connected to management server 81 via the internet.

2. Configuration of Assistance Device 10

Figure 2:
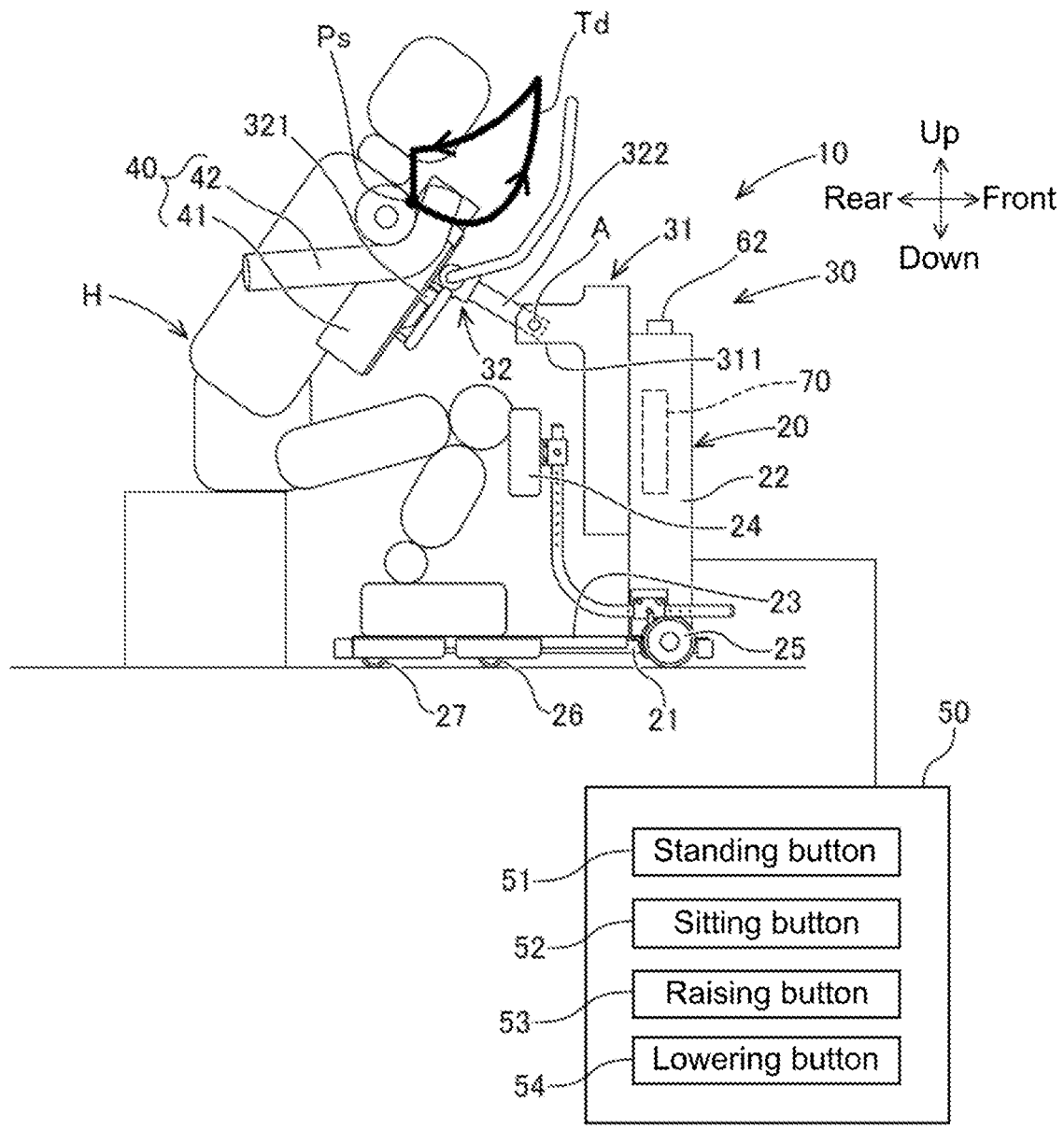
FIG. 2 is a side view of an assistance device that supports a care receiver who is seated.

Assistance device 10 assists care receiver H (refer to FIG. 2) in a standing operation of going from a sitting posture to a standing posture, and in a sitting operation of going from a standing posture to a sitting posture. By supporting the upper body of care receiver H in a standing position, assistance device 10 can be maneuvered by only one caregiver such that care receiver H can be moved, for example, to a target location in a care facility. As shown in FIGS. 1 and 2, assistance device 10 is provided with base 20, driving device 30, supporting member 40, operation device 50, detection sensor 61, microphone 62, and control device 70.

Base 20 includes support column 22 fixed to frame 21. Footrest 23 on which a care receiver H loaded on assistance device 10 can rest both feet is provided on support column 22. Also, lower limb contacting section 24 that contacts the lower limbs of care receiver H who is in a specified posture is provided on support column 22. Further, three wheels, 25 to 27, are provided respectively on both the left and right sides on a lower side of frame 21. Thus, assistance device 10 is configured to move in a front-rear direction, turn in a left-right direction, and to spin around (rotate on the spot).

Driving device 30 supports supporting member 40 that supports the upper body of care receiver H to be movable in a vertical direction and a front-rear direction of base 20. Driving device 30 is able to move supporting member 40 along a specified movement path by a combination of vertical movement of raising and lowering section 31 and rotational movement of oscillating section 32. Raising and lowering section 31 is raised and lowered by the driving of a linear motion device (not shown). A motor (not shown) for rotating oscillating section 32 is stored inside raising and lowering section 31. Oscillation support section 311 of raising and lowering section 31 supports oscillating section 32 to be rotatable around center shaft A.

Oscillating section 32 swings around center shaft A to oscillate supporting member 40. Oscillating section 32 includes oscillation main body 321, which is an attachment section for attaching and removing supporting member 40. Oscillation main body 321 is provided on a front side of arm 322 that is rotated around center shaft A by the driving of a motor. When assistance device 10 assists a standing operation, arm 322 mainly rotates forwards from a state extending to the rear. Conversely, when assistance device 10 assists a sitting operation, arm 322 mainly rotates backwards to a state extending to the rear. Oscillating section 32 oscillates supporting member 40 attached to oscillation main body 321 by arm 322 rotating around center shaft A.

Supporting member 40 is attached to oscillation main body 321 and is a member that supports the upper body of care receiver H. Supporting member 40 includes torso supporting section 41 formed with a surface that closely matches the shape of the torso of care receiver H. The supporting surface of torso supporting section 41 is formed to flexibly change shape, and contacts the front of the torso of the upper body of care receiver H to support their torso. Supporting member 40 includes a pair of underarm supporting sections 42 that support the underarms of care receiver H. The surface of the pair of underarm supporting members 42 is covered in a material that can flexibly change shape.

Operation device 50 includes multiple operation buttons corresponding to each operation for which assistance device 10 provides assistance. Specifically, operation device 50 includes standing button 51, sitting button 52, raising button 53, and lowering button 54 corresponding respectively to a standing operation, a sitting operation, a raising operation, and a lowering operation. When one of the buttons is pushed, assistance device 50 outputs a signal corresponding to the type of the button to control device 70 while the button is being pushed. The above "raising operation" refers to raising the care receiver H while maintaining the angle of their upper body. The above "lowering operation" refers to lowering the care receiver H while maintaining the angle of their upper body.

Detection sensor 61 is used to detect a state of assistance device 10. The above "state of assistance device" includes a state of a movable section (raising and lowering section 31, oscillation section 32) of assistance device 10, or a state of an operation mechanism (linear motion device, motor, or the like) in driving device 30. Here, detection sensor 61 is, for example, a linear scale provided on a linear motion device that raises and lowers raising and lowering section 31, or an encoder provided on a motor that rotates arm 322.

Also, the above "state of assistance device" includes a state of supporting member 40 that supports care receiver H. Here, detection sensor 61 is provided between, for example, oscillation main body 321 and torso supporting section 41, and is a load cell that detects the load received by supporting member 40 from care receiver H, or an ammeter that measures the current supplied to the motor that rotates oscillating section 32.

Microphone 62 records a sound arising from at least one of care receiver H and the caregiver. Sound data M1 acquired by the recording using microphone 62 is memorized on a memory section (not shown) of control device 70. Microphone 62 is provided on assistance device 10. By this, microphone 62 is configured to be able to record sounds from care receiver H and a caregiver from various positions and during movement even when assistance device 10 is moved to multiple locations such as a different room or a bathroom.

Control device 70 controls operation of raising and lowering section 31 and oscillating section 32 of driving device 30 based on operations of operation device 50. In the present embodiment, control device 70, when performing a standing operation or a sitting operation, controls movement of supporting member 40 by coordinating vertical movement of raising and lowering section 31 and rotational movement of oscillating section 32. Also, in the present embodiment, control device 70 includes analyzers, including speech analyzer 71, that configure assistance system 1. Details regarding analyzers and so on of assistance system 1 are described later.

3. Assisting a Transfer Operation Using Assistance Device 10

Assistance device 10 configured as described above assists a transfer operation of a care receiver H. The above "transfer operation" refers to a cycle of operations in which a standing operation and a sitting operation are performed in order. However, among the cycle of operations, operations unrelated to an operation for assisting care receiver H, for example, such as a test for checking operation of a movable section (raising and lowering section 31, oscillating section 32) are not included in a transfer operation.

Assistance device 10, during a transfer operation, supports a body part of care receiver H (for example, the upper body of care receiver H), and after assisting a standing operation of care receiver H who is in a sitting posture, performs a change of direction, and assists in a sitting operation in which care receiver H sits down again at a different position. This transfer operation is performed with a purpose of, for example, transferring between a bed and a wheelchair in the same room, or transferring from a bed of one room to the toilet in a restroom.

Here, the upper limit of a portion of torso supporting section 41 that contacts a torso is reference position Ps. The thick solid lines in FIG. 2 represent movement path Td of reference position Ps during a standing operation or a sitting operation of the transfer operation of care receiver H. In other words, control device 70 controls movement of supporting member 40 by coordinating vertical movement of raising and lowering section 31 and rotational movement of oscillating section 32 such that reference position Ps moves along movement path Td shown in FIG. 2.

Figure 7:
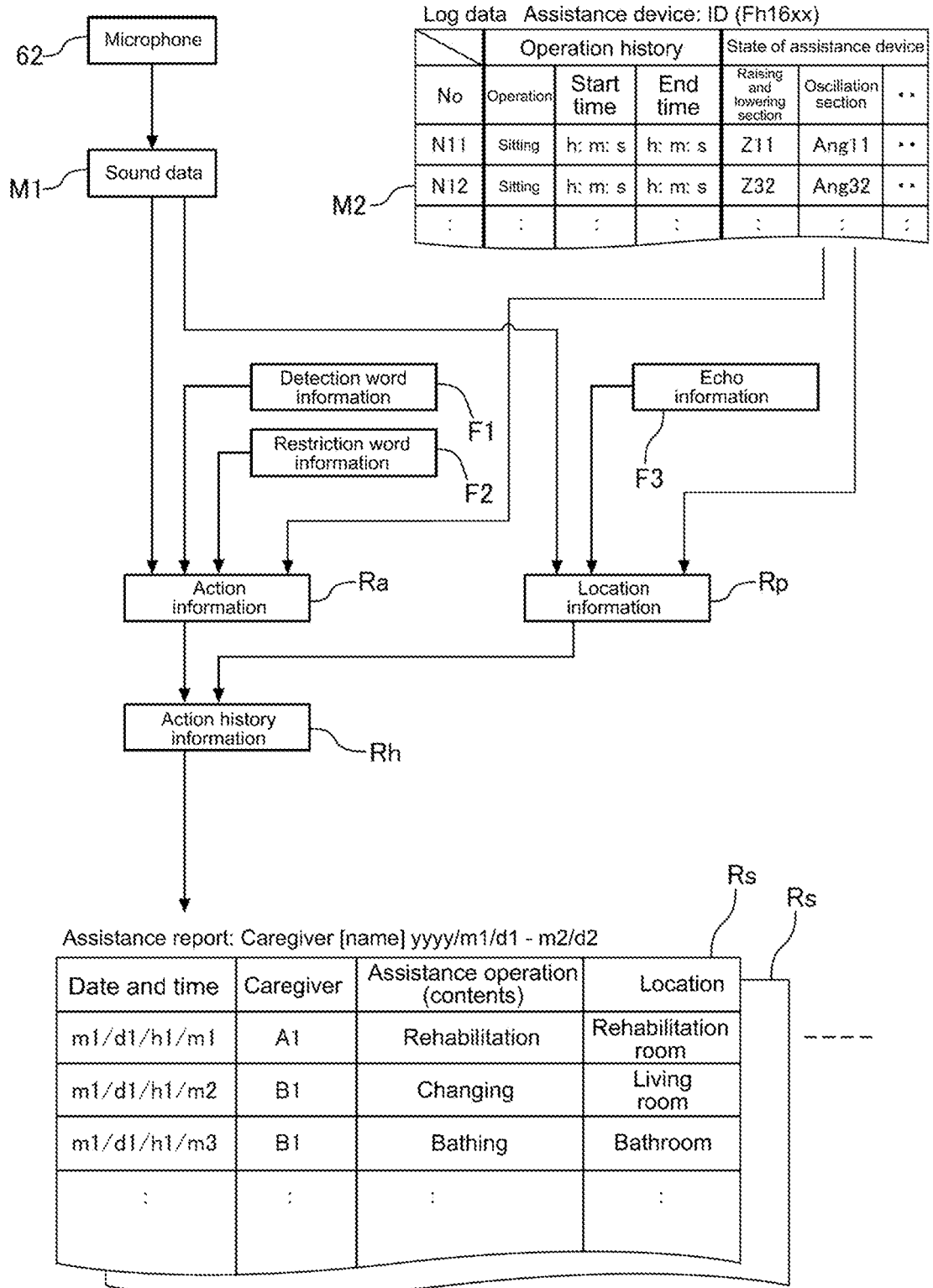
FIG. 7 shows results of each type of analysis processing and an assistance report.

Here, control device 70 of assistance device 10 records log data M2 from which it is possible to trace operation of assistance device 10. As shown in FIG. 7, included in "log data M2" is operation history of each type of operation including a standing operation and a sitting operation. In the present embodiment, included in log data M2 are the time, operation history, and state of assistance device.

The above "operation history" includes the start time and the end time of the operation of driving device 30 actually controlled by control device 70 in accordance with each type of operation of operation device 50. The "state of assistance device" included in log data M2 includes a state of a movable section (raising and lowering section 31, oscillating section 32), or a state of an operation mechanism (linear motion device, motor, or the like) in driving device 30.

A state of a movable section includes, for example, a position of raising and lowering section 31 in the vertical direction, or an angle of oscillating section 32. These are obtained based on detection results of detection sensor 61 such as, for example, a linear scale provided on a linear motion device that raises and lowers raising and lowering section 31, or an encoder provided on a motor that rotates arm 322. A state of an operation mechanism includes, for example, a current value supplied to the above linear motion device or motor. The above current value varies in accordance with the load during performance of each type of operation.

Also, "state of assistance device" included in log data M2 may be the load received from care receiver H by supporting member 40 that supports care receiver H. The load received from care receiver H by supporting member 40 varies in accordance with the body weight and leg power of care receiver H, the posture of care receiver H, and the like. The load received from care receiver H by supporting member 40 is obtained based on, for example, a detection result of detection sensor 61 such as a load cell provided between oscillation main body 321 and torso supporting section 41, or a current value supplied to a motor that rotates oscillating section 32.

4. Detailed Configuration of Assistance System 1

Assistance system 1, in a location where assistance is performed such as a care facility, records contents of various types of assistance actually given to a care receiver as action history information Rh. Action history information Rh recorded by assistance system 1, for example, is sent as an assistance report to a manager or caregiver of the care facility, or to family of the care receiver, and can be used to increase the quality of and improve the assistance provided to care receivers. In the present embodiment, a portion of assistance system 1 is built into assistance device 10, and performs specified assistance support processing.

Here, from the perspective of being able to accurately grasp the contents of assistance that a care receiver has received, it may be considered to provide cameras in the care facility. However, capturing video with a camera, along with images, records operations and sounds not required in a record of an assistance report, so is not desirable from the viewpoint of protecting privacy. Thus, assistance system 1 of the present embodiment allows assistance operations to be understood without capturing video, employing a configuration that allows assistance operations actually performed to be understood using speech data.

Specifically, as shown in FIG. 1, assistance system 1 is provided with speech analyzer 71, echo analyzer 72, log data analyzer 73, action history information generator 74, report generator 75, and report sending section 76. Speech analyzer 71 acquires information related to an action (also referred to as "action information Ra") after analyzing speech of at least one of a caregiver or care receiver H included in sound data M1 acquired by microphone 62. The above action information Ra is information linking the action of the movement or assistance operation (for example, bathing, rehabilitation) and so on to a time record. Action information Ra may include the name of the caregiver or care receiver H related to the action.

In the present embodiment, speech analyzer 71, based on a result of speech recognition processing on sound data M1, acquires action information Ra by identifying at least one of the care receiver H or the caregiver, and identifying an assistance operation for the care receiver H. The above speech recognition processing is processing that uses appropriate conventional speech recognition technology to convert speech waveforms included in sound data M1 into text. Speech analyzer 71, to improve the accuracy of conversion to text, may perform learning using many speech samples, or results of corrections to the post-conversion text made by an administrator or the like.

Further, in the present embodiment, speech analyzer 71, by detecting a specified keyword included in the result of the speech recognition processing, identifies at least one of the care receiver H and the caregiver and identifies the assistance operation. Note that, speech analyzer 71, during the above speech recognition processing, may also identify a location (for example, bathroom, rehabilitation room) at which the assistance operation was performed. In this case, speech analyzer 71 also acquires location information Rp, which is described later.

During the above speech recognition processing, speech analyzer 71, based on detection word information F1, detects a keyword included in the speech recognition processing result. At least one of the following is registered as a keyword in the above detection word information F1: name of care receiver H, name of caregiver, name of item related to assistance operation, name or verb of operation that care receiver H performs during the assistance operation. Thus, speech analyzer 71 detects a keyword when a character string included in the speech recognition processing result matches or is suitably similar to the keyword.

Here, due to assistance support processing using sound data M1 as above, compared to a configuration in which a camera is set in an assistance location, it is easier to protect the privacy of a care receiver and the like. However, similar to when a camera is provided, speech information not required in a record of action history information or an assistance report may be recorded in sound data M1. Thus, from the viewpoint of strengthening privacy protection, speech analyzer 71 of the present embodiment restricts the identification of a name or the like to certain conditions. Specifically, speech analyzer 71 checks whether a specified restricted word is included in the speech recognition processing result.

Further, speech analyzer 71, when a restriction word included in the restriction word information F2 registered in advance is detected in the speech recognition processing result, identification of the assistance operation and identification of at least one of the care receiver H or the caregiver based on the keyword detection result applied to the conversation portion including the restriction word is restricted. The above restriction word may be set as desired by a caregiver or manager, for example, to a word not likely to be usually used, so as to be used as a trigger such that the caregiver can purposefully exclude a conversation portion from the analysis.

The above "conversation portion" is a portion of conversation had by care receiver H and the caregiver in the sound data M1, for example, a summary of interaction where a period of blank space without any speech is up to a specified length. The above term "conversation" may also include a one-way interaction, for example, in which a caregiver speaks to a care receiver H. Speech analyzer 71, in a case in which a restriction keyword is detected in the speech recognition result, does not perform identification of the care receiver H or the like even if a keyword is included in the conversation portion, or performs identification of care receiver H or the like under a set of specific limitations.

Also, speech analyzer 71, depending on the restriction word, may selectively exclude a part of the conversation portion after the restriction word, or a part of the conversation portion before the restriction word, from the identification of the care receiver H or the like. According to the above configuration, during assistance support using sound data M1, because identification of a care receiver H or the like is restricted based on a restriction word, it is possible to more reliably protect the privacy of a care receiver H or the like.

Echo analyzer 72 analyzes an echo included in sound data M1 and obtains information related to a location (also referred to as "location information Rp"). The above location information Rp is information linking the location at which the assistance operation was performed (for example, living room, bathroom, rehabilitation room, restroom) to a time record. In the present embodiment, echo analyzer 72 identifies the room in which microphone 62 recorded the speech based on a specified reflection sound frequency or reverberation time (a time until a repeated sound decays to a specified amplitude) in the sound data M1.

Specifically, echo analyzer 72 calculates a width of the room based on the reflection sound frequency or reverberation time, and identifies the room in which the speech was recorded from the calculation result. In the present embodiment, echo analyzer 72 identifies the location at which microphone 62 recorded the speech using echo information F3 that represents a location (room, corridor, or the like) in a care facility and a sound reflection frequency or reverberation time. Note that, echo analyzer 72 may identify an assistance operation (for example, bathing or rehabilitation) based on the room (for example, bathroom or rehabilitation room) identified in the above manner.

Log data analyzer 73 acquires action information Ra by identifying an assistance operation with respect to care receiver H based on log data M2 recorded by assistance device 10. In the present embodiment, in log data M2, log data analyzer 73 detects a transfer operation in which, to transfer care receiver H, a standing operation and a sitting operation are performed in order, or detects movement between different rooms, and identifies the assistance operation based on the detection result. Details regarding log data analysis processing are described later.

Action history information generator 74 generates action history information Rh of at least one of the caregiver or care receiver H based on action information Ra and location information Rp. The above action history information Rh is information that combines action information Ra and location information Rp generated by each type of analysis processing from sound data M1 and that links the location, action of the assistance operation or the like, care receiver H, and caregiver identified by the recording time. Here, multiple candidates may be recorded in action information Ra and location information Rp in a case in which it is not possible to identify a single action or location. In such a case, action history information generator 74 may be combined such that the respective information is interpolated by appropriately selecting from the above candidates based on particular items included in action information Ra and location information Rp.

Report generator 75 generates assistance report Rs including contents of assistance operations received by care receiver H based on action history information Rh generated by action history information generator 74. In the present embodiment, report generator 75 generates an assistance report Rs for each of the multiple care receivers H. As shown in FIG. 7, assistance report Rs of a care receiver H records time, caregiver, assistance operation, and location. Note that, for items that could not be identified by each analysis of sound data M, multiple candidates or a blank field are recorded in assistance report Rs.

Report sending section 76 sends assistance report Rs for a care receiver H to terminal device 82 owned by a relative of care receiver H. In the present embodiment, report sending section 76 sends assistance report Rs via management server 81, which is described later. Specifically, report sending section 76 uploads assistance report Rs generated by report generator 75 to management server 81. By this, assistance reports Rs linked to a given care receiver H are accumulated on management server 81. Management server 81 sends corresponding assistance reports Rs related to a care receiver H to terminal device 82 in accordance with requests from the terminal device.

Note that, assistance reports Rs generated by report generator 75, as well as being generated for each of the multiple care receivers H as above, may be generated for each of the caregivers, assistance devices 10, assistance operations, or locations. In such cases, for example, report sending section 76 sends the assistance reports Rs generated for a caregiver or an assistance device 10 in accordance with a request from a manager of the care facility. Thus, the manager of the care facility can appropriately evaluate the ability of a caregiver, and make effective use of assistance devices 10.

5. Configuration of Management Server 81

As shown in FIG. 1, management server 81 is a cloud server, and is capable of communicating with multiple clients (for example, multiple assistance devices 10 or multiple terminal devices 82) via the internet. Management server 81 memorizes assistance reports Rs (refer to FIGS. 1 and 7) uploaded from multiple assistance devices 10. In the present embodiment, assistance reports Rs are generated for each of the multiple care receivers H. Management server 81 coordinates with report sending section 76 to send assistance reports Rs to terminal device 82 or the like.

6. Assistance Support Processing by Assistance System 1

Assistance support processing by assistance system 1 will be described referring to FIGS. 3 to 7. Here, for example, assistance support processing may be performed periodically or as determined by a manager of assistance system 1. Note that, sound data M1 recorded by microphone 62 and log data M2 recorded by control device 70 over a specified period are memorized on a memory section of control device 70 of assistance device 10.

Figure 3:
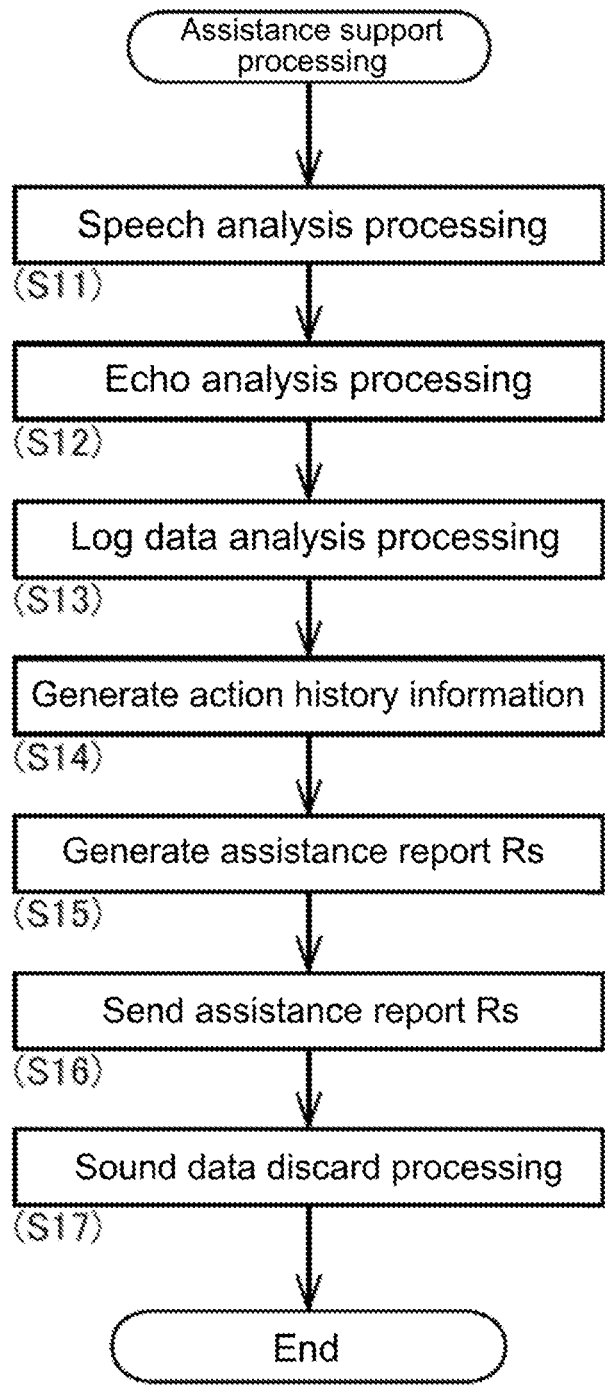
FIG. 3 is a flowchart showing assistance support processing.
Figure 4:
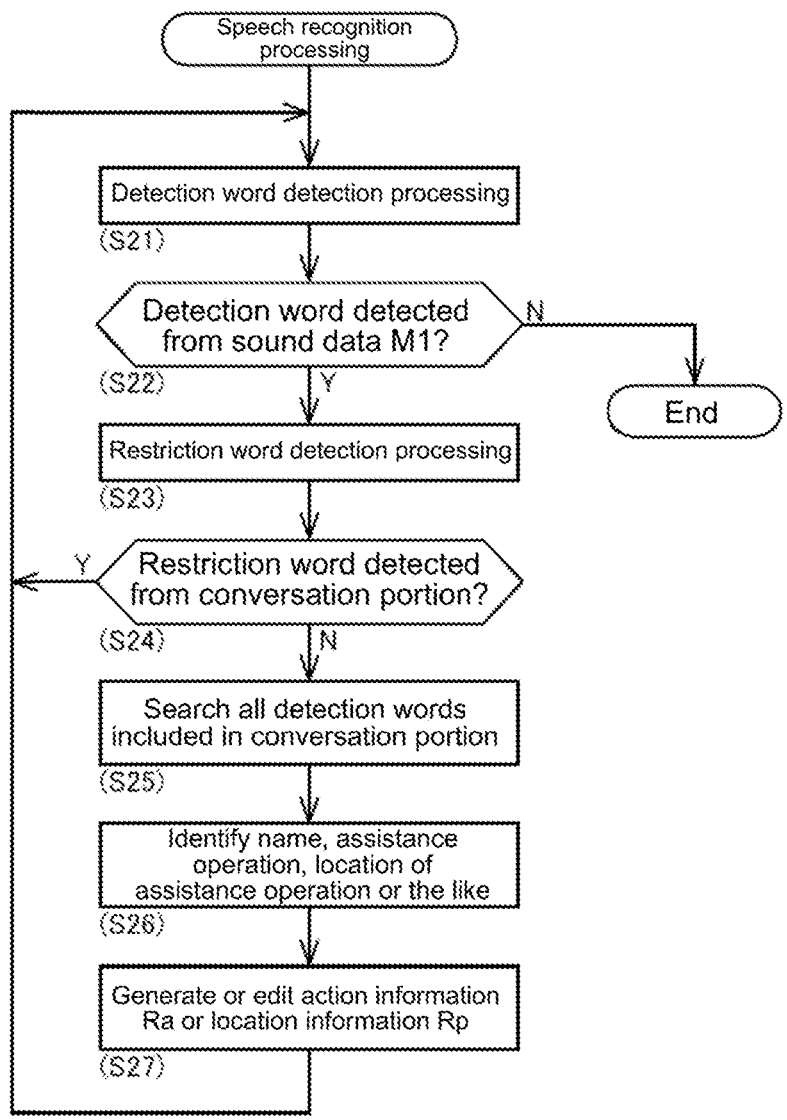
FIG. 4 is a flowchart showing speech recognition processing.

As shown in FIG. 3, speech analyzer 71 performs speech analysis processing on sound data M1 (S11). In the present embodiment, speech analyzer 71 performs speech recognition processing as the speech analysis processing to acquire action information Ra. In detail, speech analyzer 71, during speech recognition processing, as shown in FIG. 4, performs search processing of a detection word included in detection word information F1 in order from the start of sound data M1 (S21). If a detection word is detected (S22: yes), speech analyzer 71 performs search processing on at least one restriction word included in restriction word information F2 during the conversation portion that included the detection word (S23).

If no restriction word is detected in the conversation portion (S24: no), speech analyzer 71 searches all the detections words included in the conversation portion (S25). Then, speech analyzer 71 identifies the name of the care receiver H, the name of the caregiver, the assistance operation, the location of the assistance operation, and the like based on the detected detection word (S26). Speech analyzer 71 links the item identified in S26 to the time and generates or edits action information Ra or location information Rp (S27).

In a case in which a restriction word is detected from the conversation portion (S24: yes), speech analyzer 71 omits processing of identifying the name of care receiver H or the like based on the search of the detection word and the detection result of the applicable conversation portion (S25 to S27). Speech analyzer 71 performs a keyword search until the end of sound data M1 (S21), and if a keyword is not detected (S22: no), ends speech recognition processing.

Figure 5:
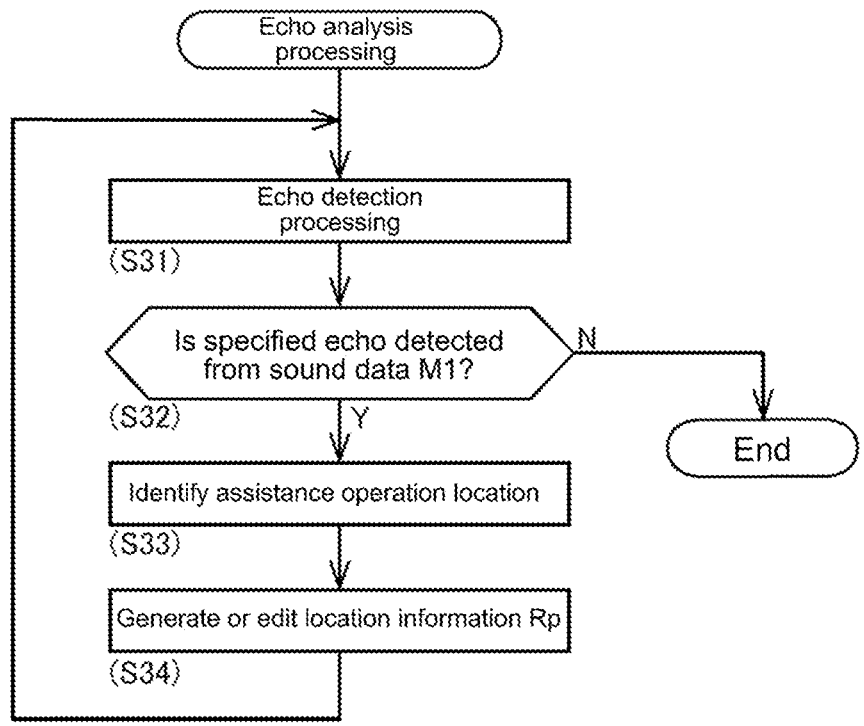
FIG. 5 is a flowchart showing echo analysis processing.

Next, as shown in FIG. 3, echo analyzer 72 performs echo analysis processing on sound data M1 (S12) and acquires location information Rp. In detail, echo analyzer 72, during echo analysis processing, as shown in FIG. 5, performs search processing of an echo included in echo information F3 in order from the start of sound data M1 (S31). In a case in which a specified echo is detected by the search processing (S32: yes), echo analyzer 72 identifies a room in which the speech was recorded by microphone 62 based on a specified reflection sound frequency and echo information F3 (S33).

Note that, in a case in which relationships between reverberation times and locations are set in echo analyzer 72, echo analyzer 72 performs search processing of the specified reverberation time from sound data M1, and identifies the location at which microphone 62 recorded the speech based on the reverberation time and the echo information F3. In a case in which relationships between rooms and both the reflection sound frequency and reverberation time are set, echo analyzer 72 may set the location based on the reflection sound frequency and the reverberation time.

Continuing, echo analyzer 72 identifies an assistance operation for a care receiver H based on the location identified in S33 (S34). However, in cases in which the assistance operation cannot be identified such as if the identified location is the living room of the care receiver H, identification of the assistance operation may be omitted, or several candidates may be presented. Echo analyzer 72 links the items identified in S33 and S34 to a time and generates or edits location information Rp (S35). Echo analyzer 72 performs a search of reflection sound until the end of sound data M1 (S31), and if a reflection sound is not detected (S32: no), end echo analysis processing.

Figure 6:
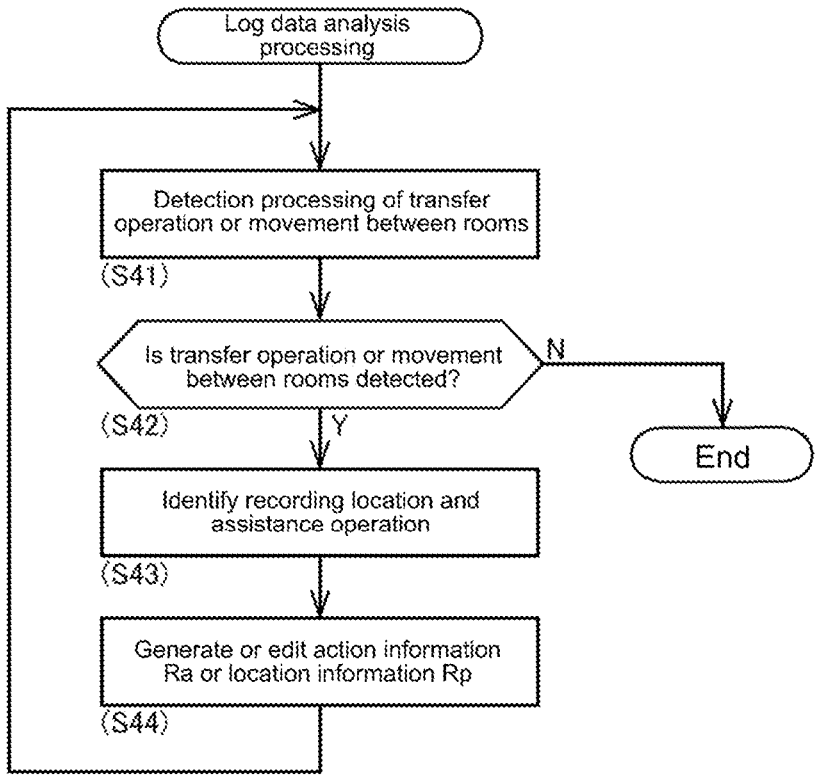
FIG. 6 is a flowchart showing log data analysis processing.

Continuing, as shown in FIG. 3, log data analyzer 73 performs log data analysis processing on log data M2 (S13) and acquires action information Ra. In detail, log data analyzer 73, during log data analysis processing, as shown in FIG. 6, performs search processing in log data M2 of a transfer operation in which, to transfer care receiver H, a standing operation and a sitting operation are performed in order, or of a movement between different rooms (S41). Here, operation history recorded in log data M2 includes operation and controls related to testing and the like performed in a state without a care receiver H loaded on the assistance device, in addition to transfer operations where a care receiver was actually loaded. Here, log data analyzer performs search processing of a transfer operation.

Specifically, log data analyzer 73 searches in log data M2 for an operation cycle of a standing operation and a sitting operation performed in order. Here, the operation cycle may include an adjustment operation performed as part of a series related to at least one of the standing operation and the sitting operation. The above adjustment operation may include, for example, a raising and lowering operation of support member 40 performed during the standing operation, or a rotation operation of support member 40 performed during unloading of the care receiver H.

Log data analyzer 73 determines whether the detected operation cycle is a transfer operation that transferred the care receiver H. In the present embodiment, log data analyzer 73 calculates the interval between a standing operation and a sitting operation during the operation cycle, in detail, the time from the end of the standing operation to the start of the sitting operation (referred to as the "intermediate time"). Next, log data analyzer 73, in a case in which the intermediate time is within a specified time, determines that the operation cycle is a transfer operation. Log data analyzer 73 may perform determination based on a detection result of detection sensor 61.

Here, in a case in which the transfer operation was performed with the care receiver H riding on assistance device 10 for some purpose other than testing assistance device 10, this is taken to mean that processing was performed with a purpose of the transfer operation being such as changing direction or moving after completing the standing operation, or removing clothing of care receiver H or the like. As a result, an intermediate time equal to the time required for the above processing arises. On the other hand, if the intermediate time is excessively long (the intermediate time exceeds the specified time), it is determined, for example, that assistance device 10 is in a state of being stored. Thus, log data analyzer 73 determines whether the operation cycle is a transfer operation based on the length of the intermediate time.

Log data analyzer 73, in addition to searching for a transfer operation as described above, searches for movement between different rooms using assistance device 10. Specifically, log data analyzer 73 recognizes movement by the traveling of assistance device 10 based on a detection result of detection sensor 61 included in log data M2. The above detection sensor 61 may be an accelerometer provided on assistance device 10. By this, log data analyzer 73 searches for movement between different rooms.

Next, in a case in which a transfer operation or movement between rooms is detected from log data M2 (S42: yes), log data analyzer 73 identifies the location and the assistance operation from when microphone 62 recorded the speech based on the detection result (S43). However, in a case in which a single room or single assistance operation cannot be identified, several candidates of rooms or assistance operations may be presented. Log data 73 links the item identified in S43 to the time and generates or edits action information Ra or location information Rp (S44).

Log data analyzer 73 performs search processing (S41) of a transport operation and repeats S42 to S44 until the end of log data M2 (S41). By this, an item identified in accordance with a detected transfer operation or the like is memorized on action information Ra or location information Rp. Log data analyzer 73, in a case in which search processing (S41) of a transfer operation or the like ends after reaching the end of log data M2 without a transfer operation or the like being detected (S42: no), log data analysis processing ends.

Action history information generator 74 combines location information Rp and action information Ra generated or edited by each type of analysis processing (speech recognition processing, echo analysis processing, log data analysis) to, as shown in FIG. 7, generate action history information Rh (S14). Further, report generator 75 generates assistance reports Rs for each of the multiple care receivers H based on the action history information Rh (S15). Generated assistance reports Rs are, for example, uploaded to management server 81.

Report sending section 76, in accordance with a request from a terminal device, sends the applicable assistance report Rs related to a care receiver H to the terminal device 82 via management server 81 (S16). Also, assistance system 1 performs discarding processing on sound data M1 used in each analysis processing during the above assistance support processing (S17). By this, personal information that may be included in each type of data is discarded such that the privacy of care receivers H and caregivers is reliably protected.

7. Effects of Embodiments

In an embodiment above, assistance system 1 includes: assistance device 10 configured to assist movement of a care receiver H; microphone 62 provided on assistance device 10; speech analyzer 71 configured to analyze speech of at least one of a caregiver or the care receiver included in sound data M1 acquired by the microphone and acquire information Ra related to an action; echo analyzer 72 configured to analyze an echo included sound data M1 and acquire information Rp related to a location; and action history information generator 74 configured to generate action history information Rh of at least one of the caregiver or the care receiver H based on the information Ra related to the action and the information Rp related to the location.

According to such a configuration, because an image of assisting the care receiver is not stored, it is possible to protect the privacy of the care receiver H and the caregiver. Also, because an action history is recorded for at least one of the care receiver H and the caregiver, it is possible to understand an assistance operation for the care receiver H and to assist in providing more appropriate care. Also, during an assistance operation using assistance device 10, speech is reliably recorded using microphone 62 provided on assistance device 10. Thus, it is possible to reliably identify care receiver H and the like.

8. Alternative Embodiments 8.1. Speech Analysis

In an embodiment above, speech analyzer 71 is configured to perform speech recognition analysis (refer to FIG. 4) as speech analysis processing (S11). However, speech analyzer 71 may acquire action information Ra by performing voiceprint analysis processing as speech analysis processing instead of speech recognition processing. In such a configuration, speech analyzer 71 acquires information Ra related to actions by identifying at least one of a care receiver H and a caregiver based on a voiceprint extracted from sound data M1 and voiceprint information F4 (refer to FIG. 9) representing a voiceprint of a caregiver and a voiceprint of a care receiver H. The above voiceprint information F4 is a voiceprint of a caregiver and the like registered in advance by recording speech voice using microphone 62.

Figure 8:
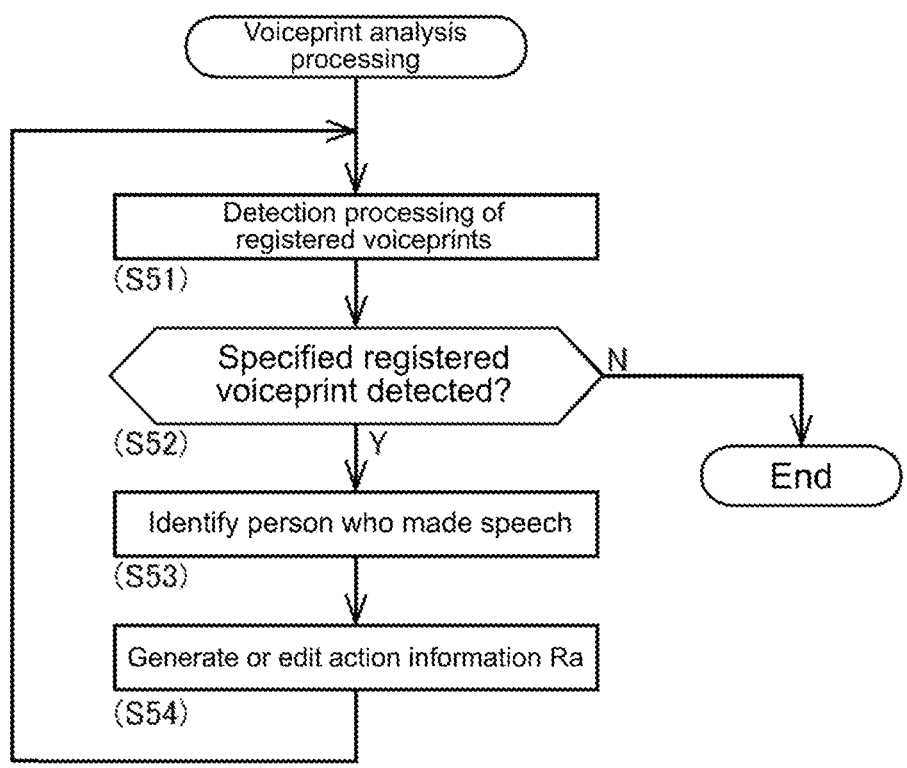
FIG. 8 is a flowchart showing voiceprint analysis processing of an alternative embodiment.

In detail, speech analyzer 71, during voiceprint recognition processing, as shown in FIG. 8, in order from the start of sound data M1, performs search processing of a registered voiceprint that matches or is suitably similar to a voiceprint included in voiceprint information F4 (S51). Next, in a case in which a specified registered voiceprint is detected from sound data M1 (S52: yes), speech analyzer 71 identifies the person who made the speech (caregiver or care receiver H) when the speech was recorded by microphone 62 based on the detected specified voiceprint and voiceprint information F4 (S53).

Speech analyzer 71 links the item identified in S53 (name of caregiver or the like) to the time and generates or edits action information Ra (S54). Speech analyzer 71 performs search processing (S51) of registered voiceprints and repeats S52 to S54 until the end of sound data M1. By this, names of caregivers and the like identified according to the detected voiceprints are recorded in action information Ra. Speech analyzer 71, in a case in which search processing of registered voiceprints until the end of sound data M1 has been completed (S51) and no registered voiceprint was detected (S52: no), ends voiceprint analysis processing.

Figure 9:
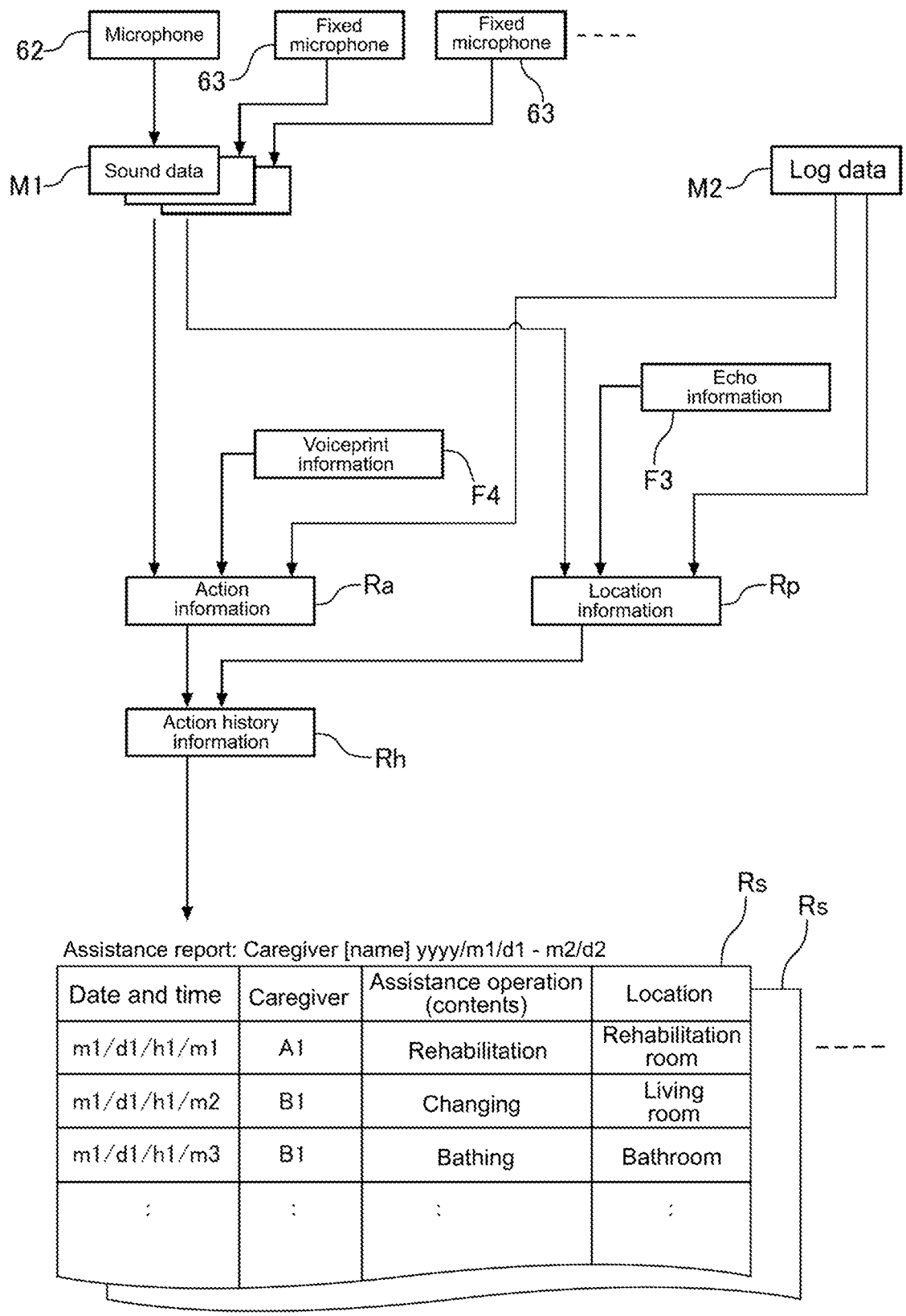
FIG. 9 shows results of each type of analysis processing and an assistance report.

Action history information generator 74 combines location information Rp and action information Ra generated or edited by each type of analysis processing including voiceprint analysis processing to, as shown in FIG. 9, generate action history information Rh (S14). According to such a configuration, it is possible to identify a care receiver H or a caregiver based on the detected voiceprint and voiceprint information F4. Thus, the identification accuracy of a care receiver H or caregiver who made a speech is improved.

8-2. Recording of Sound Data M1

In an embodiment above, microphone 62 of assistance system 1 is provided on assistance device 10. However, assistance system 1 may be configured such that microphone 62 is provided somewhere other than assistance device 10. Specifically, microphone 62 may be provided on care receiver H or a caregiver. Also, assistance system 1 may be further provided with fixed microphone 63 (refer to FIG. 9) on a room (living room of care receiver H or rehabilitation room) or a corridor of the care facility in which the care operation is performed.

With such a configuration, speech analyzer 71 and echo analyzer 72 analyze sound data M1 acquired by fixed microphone 63. Accordingly, speech analyzer 71 and echo analyzer 72 can identify each item based on sound data M1 recorded by both microphone 62 provided on assistance device 10 and multiple fixed microphones, thereby acquiring even more reliable action information Ra and location information Rp.

8-3. Configuration of Assistance System 1

In an embodiment above, analyzing sections and the like of assistance system 1 (speech analyzer 71, echo analyzer 72, log data analyzer 73, action history information generator 74, report generator 75, report sending section 76) are built into control device 70 of assistance device 10. However, at least a portion of the analyzing sections and the like of assistance system 1 may be configured as separate devices, so long as acquisition of sound data M1 recorded by microphone 62 or fixed microphone 63 is possible. For example, analyzing sections and the like may be configured to be provided in one of a management computer provided in a management room of the care facility, management server 81 on a network, or terminal device 82 owned by family of care receiver H.

Here, sound data M1 and log data M2 have a large data volume compared to action history information Rh generated by action history information generator 74 and assistance reports Rs generated by report generator 75, so require longer to send. Therefore, it is preferable to provide speech analyzer 71, echo analyzer 72, and log data analyzer 73 inside the care facility relatively close to microphone 62 and fixed microphone 63.

Also, for example, management server 81 may manage only multiple assistance devices 10 in the care facility, instead of using a cloud server connected via the internet. Further, assistance system 1, for example, may be configured without management server 81. For example, assistance system 1 may be configured from assistance device 10 capable of communicating with terminal device 82.

8-3. Assistance Device 10

In an embodiment above, base 20 of assistance device 10 used by a caregiver to assist a care receiver H is provided with footrest 23 on which care receiver H rests both feet. With such an assistance device 10, in a state with the upper body of care receiver H supported by support member 40, a portion of the body weight of the care receiver H is received by footrest 23. Thus, assistance device 10 can transfer a care receiver H who does not have the leg power required to stand up or walk. However, for example, the assistance device does not require footrest 23, and care receiver H may support a portion of their body weight when moving using their own legs, such that care receiver H is assisted when walking.

REFERENCE SIGNS LIST

1: assistance system; 10: assistance device; 62: microphone; 63: fixed microphone; 70: control device; 71: speech analyzer; 72: echo analyzer; 73: log data analyzer; 74: action history information generator; 75: report generator; 76: report sending section; 81: management server; 82: terminal device; H: care receiver; M1: sound data; M2: log data; F1: detection word information; F2: restriction word information; F3: echo information; F4: voiceprint information; Ra: action information (information related to an action); Rp: location information (information related to a location); Rh: action history information; Rs: assistance report

The invention claimed is:

1. An assistance system comprising: an assistance device configured to assist movement of a care receiver; a microphone provided on the assistance device; a speech analyzer configured to analyze speech of at least one of a caregiver or the care receiver included in sound data acquired by the microphone and acquire information related to an action by performing search processing of a detection word included in detection word information in order from a start of sound data, when the detection word is detected, performing search processing on a restricted word included in restriction word information during a conversation portion that included the detection word, when no restriction word is detected in the conversation portion, searching all detection words included in the conversation portion, identifying information including at least one of the caregiver or the care receiver, and an assistance operation for the care receiver, and linking the identified information to the information related to the action, and when the restriction word is detected in the conversation portion, omitting processing of the identified information; an echo analyzer configured to analyze an echo included in the sound data and acquire information related to a location by performing search processing of a specified echo included in echo information in order from the start of sound data, and when the specified echo is detected by the search processing, identifying a room in which the speech was recorded by the microphone based on a specified reflection sound frequency and echo information as the information related to the location; a log data analyzer configured to acquire the information related to the action by identifying the assistance operation of the care receiver based on log data in which an operation history of the assistance device is recorded including a standing operation and a sitting operation of the care receiver by performing search processing of the log data of a transfer operation in which the standing operation and the sitting operation are performed in order, or of a movement between different rooms, and when the transfer operation or the movement between different rooms is detected by the search processing, identifying information including the location and the assistance operation from when the microphone recorded the speech based on the search processing, and linking the identified information of the caregiver or the care receiver to the information related to the action and the information related to the location: an action history information generator configured to generate action history information of at least one of the caregiver or the care receiver based on the information related to the action and the information related to the location generated by the speech analyzer, the echo analyzer, and the log data analyzer: and a report generator configured to generate an assistance report including contents of assistance operations received by the care receiver based on the action history information generated by the action history information generator, wherein the assistance system is configured to perform discarding processing on the sound data used by the speech analyzer, the echo analyzer, and the log data analyzer after the assistance report is generated, the action history information includes a context in which the caregiver uses the assistance device to assist the movement of the care receiver, and the context in which the caregiver used the assistance device to assist the movement of the care receiver is different from operations performed by the assistance device to assist the movement of the care receiver.

2. The assistance system according to claim 1, wherein the speech analyzer is configured to acquire the information related to the action by identifying at least one of the care receiver and the caregiver based on a voiceprint extracted from the sound data and voiceprint information representing a voiceprint of the caregiver or a voiceprint of the care receiver.

3. The assistance system according to claim 1, wherein the action history information generator is configured to generate the action history information without capturing an image of assisting the care receiver.

4. The assistance system according to claim 1, further including a fixed microphone provided in a room or a corridor in a care facility in which the assistance operation is performed,
   wherein the speech analyzer and the echo analyzer are configured to analyze sound data acquired by the fixed microphone.

5. The assistance system according to claim 1, wherein
   the report generator is configured to generate the assistance report for each of multiple of the care receivers, and
   the assistance system further includes a report sending section configured to send the assistance report related to the care receiver to a terminal device possessed by a person concerned with the care receiver.

6. The assistance system according to claim 1, wherein the conversation portion is less than a whole of the conversation.

7. The assistance system according to claim 1, wherein the restriction word is a word not likely to be used in the context in which the caregiver uses the assistance device to assist the movement of the care receiver.

* * * * *